United States Patent [19]

Viner

[11] Patent Number: 6,166,032
[45] Date of Patent: *Dec. 26, 2000

[54] METHOD FOR CONTROLLING TOBACCO USE AND ALLEVIATING WITHDRAWAL SYMPTOMS DUE TO CESSATION OF TOBACCO USE

[75] Inventor: Norman Viner, Ottawa, Canada

[73] Assignee: Synapse Pharmaceuticals International, Inc., Ottawa, Canada

[*] Notice: This patent is subject to a terminal disclaimer.

[21] Appl. No.: 08/797,251

[22] Filed: Feb. 7, 1997

[51] Int. Cl.$^7$ .................. A61K 31/445; A61K 31/15; A61K 31/44; A61K 31/55

[52] U.S. Cl. .................. 514/316; 514/291; 514/304; 514/343; 514/344; 514/640; 514/641; 514/218; 514/280; 514/318

[58] Field of Search .................. 514/640, 641, 514/343, 344, 304, 291, 813, 318, 280, 316

[56] References Cited

U.S. PATENT DOCUMENTS

| | | | |
|---|---|---|---|
| 2,816,113 | 10/1957 | Wilson et al. | 260/296 |
| 2,996,510 | 8/1961 | Green | 260/294.8 |
| 3,063,901 | 11/1962 | O'Leary et al. | 514/304 |
| 3,077,476 | 2/1963 | Hackley, Jr. et al. | 546/264 |
| 3,852,294 | 12/1974 | Hagedorn | 260/296.47 |
| 3,877,468 | 4/1975 | Lichtneckert et al. | 131/270 |
| 3,901,248 | 8/1975 | Lichtneckert et al. | 131/2 |
| 3,928,594 | 12/1975 | Cook | 424/263 |
| 4,002,760 | 1/1977 | Cook | 424/363 |
| 4,255,439 | 3/1981 | Cooper | 424/273 R |
| 4,352,810 | 10/1982 | Benschop et al. | 424/263 |
| 4,555,397 | 11/1985 | Bachynsky | 424/10 |
| 4,596,706 | 6/1986 | Revici | 424/10 |
| 4,597,961 | 7/1986 | Etscorn | 424/28 |
| 4,675,326 | 6/1987 | Amitai et al. | 514/304 |
| 4,713,391 | 12/1987 | Chiang et al. | 548/452 |
| 4,800,204 | 1/1989 | Mueller | 514/267 |
| 4,806,356 | 2/1989 | Shaw | 424/440 |
| 4,832,994 | 5/1989 | Fey | 428/48 |
| 4,865,837 | 9/1989 | Harris, III et al. | 424/10 |
| 4,925,856 | 5/1990 | Harris, III et al. | 514/341 |
| 4,988,710 | 1/1991 | Olney | 514/318 |
| 4,999,382 | 3/1991 | Wurtman et al. | 514/646 |
| 5,021,457 | 6/1991 | Akin et al. | 514/653 |
| 5,051,426 | 9/1991 | Parnell | 514/263 |
| 5,206,371 | 4/1993 | Powers et al. | 546/290 |
| 5,362,496 | 11/1994 | Baker et al. | 424/435 |
| 5,409,946 | 4/1995 | Garvey et al. | 514/372 |
| 5,480,651 | 1/1996 | Callaway | 424/464 |
| 5,549,906 | 8/1996 | Santus | 424/440 |
| 5,574,052 | 11/1996 | Rose et al. | 514/343 |
| 5,592,956 | 1/1997 | Ju et al. | 131/270 |
| 5,593,684 | 1/1997 | Baker et al. | 424/135 |
| 5,599,554 | 2/1997 | Majeti | 424/448 |
| 5,760,049 | 6/1998 | Viner | 514/291 |

FOREIGN PATENT DOCUMENTS

| | | |
|---|---|---|
| 2016920 | 10/1979 | United Kingdom . |
| 91/09599 | 7/1991 | WIPO . |

OTHER PUBLICATIONS

Simon et al, "Administration of Obidoxime Tablets to Man", Arch. Toxicol, 36:83–88 (1976).

*Primary Examiner*—Theodore J. Criares

[57] ABSTRACT

A method for controlling tobacco use and alleviating withdrawal symptoms due to the cessation of tobacco use comprising administering to a human desiring to control tobacco use and/or suffering from withdrawal due to cessation of such use an effective amount of an acetylcholine esterase reactivator or prodrug derivative thereof optionally in association with an acetylcholine receptor antagonist.

32 Claims, No Drawings

METHOD FOR CONTROLLING TOBACCO USE AND ALLEVIATING WITHDRAWAL SYMPTOMS DUE TO CESSATION OF TOBACCO USE

BACKGROUND OF THE PRESENT INVENTION

The present invention is directed to a method for controlling tobacco use and/or alleviating the symptoms of tobacco withdrawal.

Tobacco use is recognized as constituting a significant health hazard. The particular health hazard may vary depending upon whether the tobacco use results from smoking (i.e., cigarette, cigar and pipe smoking) or from a non-smoking activity (i.e., use of smokeless or chewing tobacco). Many of the health hazards associated with the use of tobacco may be alleviated upon cessation of tobacco use. Even if not totally alleviated, many health risks associated with such use may still be reduced.

Many methods have been proposed and/or attempted to assist persons to reduce or cease tobacco use. See, for example, U.S. Pat. Nos. 3,877,468 (chewable tobacco substitute containing tobacco alkaloid); 3,901,248 (chewable tobacco substitute containing nicotine); 4,255,439 (administration of 2-imidazoline derivative in combination with an anorectic); 4,555,397 (administration of atropine and scopolamine potentiated with chlorpromazine); 4,596,706 (administration of ethylene trithiocarbonate or colloidal sulfur); 4,800,204 (administration of dopamine receptor agonist); 4,806,356 (nicotine lozenge); 4,832,994 (administration of silver acetate); 4,597,961 (transdermal administration of nicotine); 4,999,382 (administration of serotoninergic drugs); 5,021,457 (administration of phenylpropanolamine); 5,051,426 (administration of serotonin antagonist and CNS stimulant); 5,362,496 (sequential transdermal and transmucosal administration of nicotine); 5,409,946 (administration of isoxazole, isothiazole and pyrazole compounds); 5,480,651 (administration of non-specific acetylcholine agonist and a muscarinic agonist); 5,549,906 (lozenge of nicotine, nonnutritive sweetener and an absorbent excipient); 5,574,052 (administration of nicotine receptor activating drug together with antagonist to the nicotine receptor activating drug); 5,592,956 (herbs applied to acupuncture points of body); 5,593,684 (concurrent transdermal and transmucosal administration of nicotine); 5,599,554 (administration of nicotine and caffeine) and WO 91/09599 (administration of inclusion complex of nicotine and cyclodextrin). Psychiatric counseling has also been employed in an attempt to bolster the person's ability to cease or control tobacco use.

Unfortunately, none of the above methods of treatment have been very successful. While such treatments may bring short-term relief to the person, long-term success has not been easily achieved. The degree of success of such methods is generally not predictable due to the fact that the degree of success achieved is dependent upon the susceptibility of the person to the particular treatment employed. In fact, it is believed that some persons are more susceptible to the effects of tobacco use than others with the result that such persons are not easily or readily able to cease such use by means of conventional treatment methods. This is particularly believed to be the case when tobacco use begins during the teenage years and continues into adulthood. Factors such as extent of tobacco use (frequency) and type of tobacco use (smoking vs. non-smoking tobacco use) play a role in the difficulty encountered by a person upon attempting to cease or reduce the extent of tobacco use. Also, comorbid addictions, stress, psychiatric disorders and environmental factors may exacerbate the difficulty encountered by a particular person in ceasing tobacco use. It is believed, for example, that xenobiotic toxic agents such as pesticides, insecticides, fungicides, oxidants, solvents and other environmental toxins encountered by the person by various means (e.g., via drinking water and/or food impurities, etc.) may contribute to the inability of the person to cease or control tobacco use.

OBJECTS AND SUMMARY OF THE PRESENT INVENTION

It is accordingly an object of the present invention to provide a method for assisting in the cessation or control of tobacco use.

It is a further object of the present invention to provide a method for alleviating symptoms associated with reduced tobacco use.

It is still yet a further object of the present invention to provide a composition for administering to a person to assist in the control of tobacco use, as well as to reduce symptoms associated with reduced tobacco use.

In accordance with the present invention, there is accordingly provided a method for controlling tobacco use and alleviating withdrawal symptoms due to the cessation of tobacco use comprising administering to a human desiring to control tobacco use and/or suffering from withdrawal due to cessation of such use an effective amount of an acetylcholine esterase reactivator or prodrug derivative thereof optionally in association with an acetylcholine receptor antagonist.

DETAILED DESCRIPTION OF THE PRESENT INVENTION

The present invention involves the administration to a person who desires to control or cease tobacco use an effective amount of an acetylcholine esterase reactivator optionally in association with an acetylcholine receptor antagonist.

The present invention may be used to control and/or reduce tobacco use of any type. Such tobacco use may result from smoking (i.e., by cigarettes, cigars or pipes) or by use of smokeless or chewing tobacco. It has been found that of the various methods of tobacco use, chronic cigarette and smokeless or chewing tobacco use have been the most difficult to control or cease. Indeed, if begun during the teenage years, such use has been found in the past to be particularly difficult to control or cease. However, by practice of the present invention it is possible for a person who desires to control or cease such use to achieve this goal with a high likelihood of success.

The acetylcholine esterase reactivators which may be employed in the present invention are well known to those skilled in the art and well-described in the literature. Such reactivators found early use as nerve gas and toxic pesticide poisoning antidotes. Exemplary acetylcholine esterase reactivators include but are not limited to those compounds disclosed in U.S. Pat. Nos. 2,816,113; 2,996,510; 3,063,901; 3,077,476; 3,852,294; 3,928,594; 4,002,760; 4,352,810; 4,675,326; 4,865,837; 4,925,856; 4,988,710; 5,206,371 and U.K. application 2,016,920, each herein incorporated by reference in their entirety.

A preferred class of compounds which may be used as acetylcholine esterase reactivators are oximes, generally defined by the formula $(R^1-CR=NOH)^+ X^-$ where R is hydrogen, $C_{1-5}$ alkyl or $NH_2$ and $X^-$ is a pharmaceutically acceptable anion derived from a salt of an inorganic or organic acid. $R^1$ may take many forms. For example $R^1$ may be $C_{1-5}$ alkyl, aryl (e.g., phenyl), or a 5 or 6-membered heterocyclic moiety having from 1 to 3 nitrogen atoms in the heterocyclic ring.

The oxime may also be bicyclic in nature, as defined by the formula $(R^1CR=NOH\ X^-$ where R is hydrogen, $C_{1-5}$ alkyl or $NH_2$ and $R^1$ is

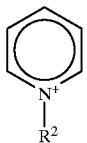

wherein $R^2$ is selected from the group consisting of:

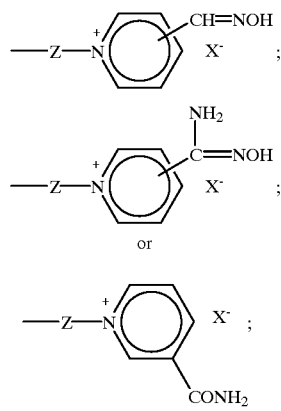

where Z is, for example, a polyalkylene group having from 1 to 6 carbon atoms, optionally including at least one ether linkage, such as $-CH_2CH_2-$, $-CH_2OCH_2-$, $-CH_2CH_2OCH_2CH_2-$, $-CH_2OCH_2CH_2OCH_2-$; or $-(CH_2)n$-phenyl-$(CH_2)n-$ where n ranges from 1 to 6 and the phenyl moiety may be substituted by $C_{1-5}$ alkyl, and wherein $X^-$ is a pharmaceutically acceptable anion derived from a salt of an inorganic or organic acid. The above formulae are intended to be merely illustrative and not limiting of the identity of the various types of oximes that may be employed in the present invention. Additional oximes not illustrated above exist which possess the ability to reactivate acetylcholine esterase and which may be employed with advantage in the present invention.

Exemplary acetylcholine esterase reactivators include the following oximes: 2-pyridine aldoxime methiodide, 4-pyridine aldoxime methiodide, methyl-2-pyridyl ketoxime methiodide, 1-methyl-pyridinium-2-aldoxime (2-PAM); 2,3-butanedione-2-oxime (DAM), pyruvaldehyde aldoxime (MINA), 2-pyridine aldoxime methochloride (2-PAM-Cl) (marketed as Protopam chloride), pralidoxime methylsulphate (marketed as Contrathion), obidoxime chloride (marketed as Toxogonin), 1,1'-polymethylene bis (4-formylpyridinium) halide oximes; 1,1'-( 2,5-dimethyl-p-phenylenedimethylene) bis (4-formylpyridinium) halide dioximes; 1,1'-polymethylene bis (3-formylpyridinium) halide dioximes; 1,11-(p-phenylenedimethylene) bis (3-formylpyridinium) halide dioximes; bis quaternary 4-formylpyriinium halide monooximes; 1,1'trimethylene bis (3-amidooximopyridinium) halides, quaternary pyridine aldoxime (TMB-4); HI-6; diacetyl monoxime; aldoxime-substituted triazolium compounds including 1,4-dimethyl-3-(hydroxyimino) methyl-1,2,4-triazolium chloride, 1-benzyl-3-(hydroxyimino)methyl-4-methyl-1,2,4-triazolium chloride, and 3-(hydroxyimino) methyl-1-methyl-4- (2'-methylsulfonyl-1'-ethyl) -1,2,4-triazolium chloride; and aldoxime-substituted imidazolium derivatives such as 1-([1'-(2'-butynyloxy)methyl]-2-(hydroxyimino) methyl-3-methylimidazolium chloride, 2-(hydroxyimino) methyl-3-methyl-1-[1'-2'-(methylsulfonyl)ethyloxy) methyl)-imidazolium chloride, 2-(hydroxyimino)methyl-3-methyl-1-[(2'-methyl-2'-nitropropyloxy)methyl]-imidazolium chloride, 1-[(2'-N,N-dimethylaminium)-1'-ethyl]2- (hydroxyimino) methyl-3-methylimidazolium chloride, 1-[2'-(hydroxyimino)methyl-3'-methyl-1'-imidazolo]-3-(4"-carbamoyl-1"-pyridino) propane dichloride, 1-(3'-bromopropyl-1'-oxy)methyl-2-(hydroxyimino) methyl-3-methylimidazolium chloride, 2-(hydroxyimino)methyl-3-methyl-1-(2'-pyrrdidinium-1'—)ethylimidazolium chloride hydrochloride, 1-(3'-butynyl-1'-thio)methyl-2-(hydroxyimino)methyl-3-methylimidazolium chloride, and 1-[(2'-N-ethyl-N-trifluoromethane sulfonyl) amino-1'-]ethyl-2-hydroxyimino)methyl-3-methylimidazolium chloride.

A preferred class of oximes suitable for use in the present invention may be depicted by the formula:

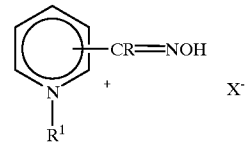

wherein R is hydrogen, $C_{1-5}$ alkyl, or $NH_2$; $R^1$ is $C_{1-5}$ alkyl (particularly methyl or ethyl), and X is an anion portion of the salt $R^1X$. Suitable acid addition salts include the chloride salt, the iodide salt and the methanesulfonate salt.

A specific oxime which is preferred for use in the present invention is 2-PAM chloride which is depicted by the following formula:

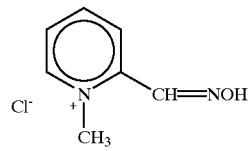

2-PAM Cl

It is also advantageous to administer prodrug derivatives of oximes as disclosed in U.S. Pat. Nos. 3,929,813 and 3,962,447. Such prodrug derivatives exhibit an enhanced ability to pass the blood/brain barrier.

It is believed that oxime-carbamate and oxime carbonate derivatives of oximes as well as hydrazone, semicarbazone and acyl hydrazone derivatives of 2-formyl-1-substituted pyridinium compounds may be usefully employed as acetylcholine esterase reactivators as described in U.S. Pat. Nos. 5,124,455 and 5,206,371, herein incorporated by reference.

The acetylcholine receptor antagonists which may optionally be employed in the present invention are well known to those skilled in the art and well-described in the literature. Exemplary antagonists include but are not limited to (singly or in combination) scopolamine, homatropine, atropine, methscopolamine, methylatropine, ipratropium, methylecgonidine (MEG), mecamylamine, benactyzine, benztropine, trihexyphenidyl, biperiden, procyclidine, benzetimide, dexetimide, iaprophen and pharmaceutically acceptable derivatives thereof. See, for example, U.S. Pat. Nos. 5,011,853 and 5,552,407, herein incorporated by reference in their entirety, which disclose exemplary acetylcholine receptor antagonists. Preferred antagonists are scopolamine and ipratropium.

Acetylcholine esterase reactivators (such as 2-PAM and HI-6) have been used in conjunction with acetylcholine receptor antagonists (such as atropine) to provide in vivo protection against nerve gas agents and other organophosphate poisons. See, for example, U.S. Pat. Nos. 3,063,901; 4,713,391; 4,865,837; and 4,925,856. However, an acetylcholine esterase reactivator (optionally together with an acetylcholine receptor antagonist) has not previously been employed to alleviate the symptoms of withdrawal associated with tobacco use cessation. The amounts of the respective components required to provide the benefits of the present invention are orders of magnitude less than the amounts normally administered to provide protection against nerve gas agents or toxic organophosphate poisoning.

In addition to the acetylcholine esterase reactivator and the acetylcholine receptor antagonist, it is within the scope of the present invention to co-administer additional compounds to assist in achieving the desired result or to provide additional cooperative treatment.

For example, it is advantageous to administer a stimulant in association with the cholinesterase reactivator. A preferred stimulant is nicotine. Nicotine may be administered by any appropriate means, including nicotine gum, a nicotine patch, etc. Nicotine administration may occur prior to, during or subsequent to administration of the two compounds. It has been found that the amount of nicotine administered is less than the amount found in a patch or a stick of nicotine gum (e.g., one milligram or so, the amount not being particularly critical).

Other conventional stimulants (such as dopaminergic stimulants) may be administered in lieu of or in addition to nicotine. Such alternative stimulants include but are not limited to mineptine, Amphetimine, Amphetaminil, Bemegride, Benzphetamine, Brucine, Chorphentermine, Clofenciclan, Clortermine, Cocoa, Demanyl Phosphate, Dexoxadrol, Dextroamphetamine Sulfate (Dexedrine), Diethpropion, N-Ethylamphetamine, Ethamivan, Etifelmin, Etryptamine, Fencamfamine, Fenethylline, Fenosolone, Fenfluramine, Flurothyl, Hexacyclonate Sodium, Homocamfin, Mazindol, Megexamide, Methamphetamine, Methylphenidate, Nicotinic agonists, Nikethamide, Pemoline, Pentylenetetrazole, Phenidimetrazine, Phenmetrazine, Phentermine, Picrotoxin, Pipradrol, Prolintane, Pyrovalerone, and Tetrahydrobenzothienopyridines and mixtures thereof.

Xanthines are an additional class of compounds that may be administered in conjunction with the acetylcholine esterase reactivator and one or more of the other optional active ingredients to assist in signal modulation along the dendrite. U.S. Pat. Nos. 4,364,922; 4,980,379; 5,288,721; 5,340,813; 5,354,756; 5,440,041; 5,473,070; 5,567,704; 5,580,873; and 5,580,874 disclose exemplary xanthines which may be used in the present invention, each herein incorporated by reference. Exemplary xanthines include but are not limited to alkylxanthines such as propylxanthine and methylxanthine. Methylxanthines include 1,3,7-trimethylxanthine (caffeine), 3,7-dimethylxanthine (theobromine), 1,3-dimethylxanthine (theophylline), aminophylline, 1,8-dimethyl-3-(2-methyl-1-butyl)xanthine, 1,3-dimethyl-8-(n-propyl) xanthine, 1,4- (4-hydroxypentyl)-3,7-dimethylxanthine, and 7-(3-phenylpropenyl) theophylline. Exemplary propylxanthines include (E)-4-(1,2,3,6-tetrahydro-1,3-dimethyl-2,6-dioxo-9H-purin-8-yl)cinnamic acid and (E)-4-(1,2,3,6-tetrahydro-2,6-dioxo-1,3-dipropyl-9H-purin-8-yl)cinnamic acid. Prodrug forms of xanthines may also be employed as disclosed in U.S. Pat. Nos. 3,935,196 and 4,061,753, herein incorporated by reference. Such forms exhibit enhanced lipid solubility of the compound.

Adenosine antagonists may also be employed in conjunction with one or more of the above. Such compounds reduce the interstitial concentration of adenosine in myocardial tissue. The compounds may either be a competitive inhibitor or a substance that reduces the concentration of adenosine. A variety of compounds may be used as adenosine antagonists including xanthines (such as those discussed above), imidazopyrimidine, pyraxolopyridine, etazolate, pyrazoloquinoline and triazoloquinazoline. Exemplary adenosine antagonists are described in U.S. Pat. Nos. 4,364,922; 4,980,379; and 5,364,922, each herein incorporated by reference.

As still yet another compound which may be administered in conjunction with one or more of the above is the inhibiting neurotransmitter gamma-aminobutyric acid (GABA) or a precursor thereof such as L-glutamic acid. GABA receptor agonists and other antiepileptics may be employed such as Epival, Baclofen, Sabril, barbiturates, Gabapentin, Lamotrizine and Riluzolo.

It may also be useful to additionally administer an acetylcholine esterase inhibitor such as Phytostigmine, Neostigmine, Demecarium, Pyridostigmine, Velnacrine, Huperzine A, Tacrine, Aricept (Donepezil hydrochloride), Memric, Artane (trihexyphenidyl), Cogentin (benzotropine mesylate), Benedryl (diphenhydramine hydrochloride), Donepezil hydrochloride, etc.

It is also within the scope of the present invention to combine administration of the active ingredients with more conventional therapies such as antioxidant treatment, vitamin treatment, heavy metal antagonists such as chelating agents and bile-acid binding resins. The identity of such compounds is well known to those skilled in the art as described in Goodman & Gilman's *The Pharmacological Basis of Therapeutics,* 9th edition, 1996.

It is within the scope of the present invention to employ both pharmaceutically acceptable analogs as well as tautomers, isomers and salts of the above listed compounds. Analogs differ from the above compounds by means of added alkyl or aryl substituents, added or deleted halogen moieties, presence of differing linkages such as ether linkage, saturation or unsaturation. As to possible salts, the present invention includes within its scope salts of alkali metals, alkaline earth metals, as well as acid addition salts of hydrochloric, hydrobromic, sulfuric, sulfamic, phosphoric, acetic, propionic, succinic, glycollic, stearic, lactic, malic, tartaric, citric, ascorbic, pamoic, maleic, hydroxymaleic, phenylacetic, glutamic, benzoic, salicylic, sulfanilic, fumaric, etc.

The compounds of the present invention may be administered by any pharmaceutically acceptable means and in any pharmaceutically acceptable form. For instance, the compounds may be administered orally in the form of pills, tablets, solutions, syrups, lozenges, etc. in which the compound is the sole or co-ingredient as the active agent. The compounds may also be administered parenterally (e.g., intravenously, intramuscularly or subcutaneously) in association with a pharmaceutically acceptable carrier. Topical administration such as by transdermal patch is also acceptable. The active components may also be administered by inhalers or internasally.

Tablets or pills may contain the active ingredient(s) in admixture with conventional pharmaceutically acceptable excipients (i.e., inert diluents). Such tablets or pills may be uncoated or coated by conventional techniques to delay disintegration and absorption in the gastrointestinal tract. More specifically, such tablets or pills may include an enteric coating to ensure disintegration and absorption in the intestine. Such coatings are generally comprised of a cellulose lower fatty acid phthalate such as cellulose acetate phthalate.

In the event that the acetylcholine receptor antagonist is administered together with the acetylcholine esterase reactivator, it is preferred that the acetylcholine receptor antagonist be administered prior to the administration of the acetylcholine esterase reactivator. Such sequential administration can be accomplished, for example, by administering the respective compounds by separate sequential oral or parenteral administration. Alternatively, the respective components can be sequentially administered in the form of a lozenge, tablet or pill which contains the two components in separate layers which will dissolve or disentegrate in sequence. Such sequential administration is not required, however.

The acetylcholine esterase reactivator (and optionally the acetylcholine receptor antagonist) are employed or administered in an amount effective to reduce or prevent the physiological and psychological effects of tobacco withdrawl due to diminished or non-use of tobacco. The phrase "reduce or prevent" is intended to refer to any degree of reduction of the symptoms of withdrawal suffered by the person, as well as any degree of prevention of the suffering of such symptoms if administered prior to the onset of such symptoms. That is, the present invention may be used prophylactically as well as to treat presently existing withdrawal symptoms.

With the above in mind, the various compounds of the present invention may be administered within a wide range of dosage levels while still enabling the benefits of the present invention to be achieved. For example, the acetylcholine receptor antagonist is generally administered at a dosage level of from about 0.001 to 10 mg. The acetylcholine esterase reactivator is generally administered at a dosage level of from about 1 mg to 10 mg. Such dosage levels are based on a standard adult body weight of 70 kg. Additional components such as stimulants are generally administered in amounts of from about 0.1 to 10 mg. The xanthine component, if administered, will generally be administered in an amount of from 25 to 300 mg. Other components that may be co-administered may be administered in conventional amounts. Such dosage administrations are repeated as required to provide the desired results, with administrations being repeated every 12 to 36 hours depending upon the extent of withdrawal symptoms observed.

The present invention is illustrated by the following examples which are not intended to be limiting of the scope of the invention but merely illustrative of various preferred and specific embodiments.

EXAMPLE 1

A forty year old male with a twenty five year smoking history of moderate intensity and a desire to cease smoking cigarettes was orally administered an acetylcholine receptor antagonist (scopolamine) followed by oral administration of an acetylcholine esterase reactivator (2-PAM-Cl), each in a pharmaceutically acceptable solution. A nicotine patch was placed on the person's torso immediately prior to the administration of the two compounds. The scopolamine was administered within the dosage range of from 0.001 to 10 mg. and the 2-PAM-Cl was administered within the dosage range of from 2 to 8 mg. The person experienced a relatively immediate lack of desire to use tobacco (in this instance the smoking of cigarettes). The ability to control the desire to smoke a cigarette continued for 8 hours. Similar results were observed upon administration of the two compounds in the form of a tablet in which the two compounds were administered in sequentially dissolved layers, with the scopolamine being the outermost layer. The administration of nicotine in chewing gum form at the time of administration of the two compounds was also found to be effective.

EXAMPLE 2

A 39 year old male smoker (1–2 packs per day) with a 25–30 pack year smoking history was highly motivated to quit smoking. He was given 5 mgs of protopam on multiple occasions following either (1 mg nicotine and 0.1 mg scopolamine) or (1 mg nicotine and 0.1 mg ipratropium) via the oral mucosa by drops and gum. The individual reported that he remained withdrawal symptom free for periods of time ranging from 6–36 hours. As a followup, he was placed on a lozenge containing an outer shell of 0.1 mg of either ipratropium or scopolamine with an inner shell of protopam 2.5 mg. On a bid dosage of either lozenge combined with a nicotine patch he was able to remain smoke free without any significant withdrawal symptoms or urges to smoke for the ten day trial period.

EXAMPLE 3

A 35 year old male (1.5 pack/day smoker) with a 30 pack year smoking history was given 5 mg of protopam following 0.1 mg ipratropium and 1 mg of nicotine sub lingual (sl) before this first cigarette of the day at 8:00 a.m. He reported that he had not normally lasted more than 20 minutes upon awakening before his first cigarette of the day in the previous 5 years. On the day of this medical trial he managed until 3:00 p.m. before having his first cigarette. By 5:00 p.m. he had attempted to smoke 3 cigarettes but found them to be too strong and much less satisfying than normal. A second dose sequenced in the same fashion was administered at 6:00 p.m. with the patient stating with surprise that he felt more satisfied than with the cigarettes earlier in the day. A third dose of just protopam (5 mg) was given at 10:00 p.m. The subject reported at that time a feeling of deep satisfaction and a clarity of mind.

EXAMPLE 4

A 37 year old male smoker was desperate to quit smoking. He had a 25 pack year smoking history and continued to smoke 12 cigarettes/day. This person also suffered from Wolf Parkinson White syndrome complicated by frequent irregular rapid heart rate and intermittent atrial fibrillation. He also suffered from a chronic myofascial syndrome characterized by diffuse muscle spasms and recurrent tendonitis. The person was given 5 mg protopam (sl) following 1 mg nicotine and 0.01 mg ipratropium on 4 occasions. On each occasion he reported a release of the need for a cigarette within 1 to 2 minutes of receiving the protopam as well as an attenuation of his myofacial syndrome and improved regularity of his heart rate lasting 2 to 5 days.

EXAMPLE 5

A 24 year old female with a 10 year half pack/day smoking history stated that she smoked partially to control her weight. She was given 1 mg nicotine and 0.01 mg of ipratropium followed by 2.5 mg of protopam in sequence on 10 occasions over a period of 2 months by the oral mucosa route of administration. On each occasion she reported relief from withdrawal symptoms and a feeling of satisfaction lasting 6 to 12 hours with no side effects. The "satisfaction" was reported as deep as that of a cigarette but longer lasting. Relief of negative symptoms such as calf muscle cramps, restricted breathing (bronchospasm and bronchial secretions), nasal congestion and fatigue were also reported. On 2 occasions the sequenced drug trial was administered before lunch and dinner on separate days when the person was "due" for her next cigarette. On both occasions, she reported not only that the need for a cigarette was extinguished but that her appetite was diminished as was her cravings for sweets.

From the above description, one of ordinary skill in the art can readily ascertain the essential characteristics of the present invention. Without departing from the scope of the invention, various changes and/or modifications can be made which are still within the scope and range of equivalence-of the attached claims.

What is claimed is:

1. A method for controlling tobacco use and/or alleviating withdrawal symptoms due to the cessation of tobacco use comprising administering to a human desiring to control tobacco use and/or suffering from withdrawal due to cessation of such use an active agent comprising an acetylcholine esterase reactivator in an amount effective to control tobacco use and/or alleviate symptoms due to the cessation of tobacco use.

2. A The method of claim 1 wherein said acetylcholine esterase reactivator is administered in a pharmaceutically acceptable carrier.

3. The method of claim 1 wherein said tobacco is in the form of cigarettes.

4. The method of claim 1 wherein said tobacco is in the form of smokeless or chewing tobacco.

5. The method of claim 1 wherein said tobacco is in the form of pipe tobacco.

6. The method of claim 1 wherein said tobacco is in the form of cigars.

7. The method of claim 1 wherein said acetylcholine esterase reactivator is administered in combination with a stimulant.

8. The method of claim 1 wherein said acetylcholine esterase reactivator is 2-pyridine aldoxime methochloride.

9. The method of claim 1 wherein said acetylcholine esterase reactivator is selected from the group consisting of 1-methyl-pyridinium-2-aldoxime, 2,3-butanedione-2-oxime, pyruvaldehyde aldoxime, bis quaternary pyridine aldoxime, obidoxime, HI6, and pharmaceutically acceptable salts thereof.

10. The method of claim 7 wherein said stimulant is selected from the group consisting of nicotine, muscarine, arecoline, lobeline, cotinine, kat, nikethamide, ethamivan, bethanechol, pilocarpine, and mixtures thereof.

11. The method of claim 7 wherein said stimulant is nicotine.

12. The method of claim 1 wherein said acetylcholine esterase reactivator is defined by the formula ($R^1$—CR=NOH)$^+$ X$^-$ where R is hydrogen, $C_{1-5}$ alkyl or NH$_2$, $R^1$ is $C_{1-5}$ alkyl and X$^-$ is a pharmaceutically acceptable anion derived from a salt of an inorganic acid or a salt of an organic acid.

13. The method of claim 1 wherein said acetylcholine esterase reactivator is defined by the formula ($R^1$—CR=NOH)$^+$ X$^-$ where R is hydrogen, $C_{1-5}$ alkyl or NH$_2$, $R^1$ is aryl and X$^-$ is a pharmaceutically acceptable anion derived from a salt of an inorganic acid or a salt of an organic acid.

14. The method of claim 1 wherein said acetylcholine esterase reactivator is defined by the formula ($R^1$—CR=NOH)$^+$ X$^-$ where R is hydrogen, $C_{1-5}$ alkyl or NH$_2$ and $R^1$ is a 5 or 6 membered heterocyclic moiety having from 1 to 3 nitrogen atoms in the heterocyclic ring and X$^-$ is a pharmaceutically acceptable anion derived from a salt of an inorganic acid or a salt of an organic acid.

15. The method of claim 1 wherein said acetylcholine esterase reactivator is defined by the formula $R^1$CR=NOH)$^+$ X$^-$ where R is hydrogen, $C_{1-5}$ alkyl or NH$_2$ and $R^1$ is

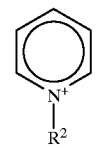

wherein $R^2$ is selected from the group consisting of;

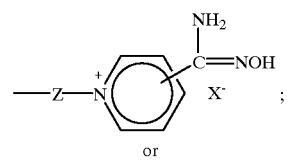

or

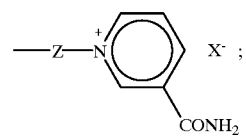

where Z is a polyalkylene group having from 1 to 6 carbon atoms, optionally including at least one ether linkage, or —(CH$_2$) n-phenyl-(CH$_2$)n— where n ranges from 1 to 6 and the phenyl moiety may be optionally substituted by $C_{1-5}$ alkyl, and wherein X$^-$ is a pharmaceutically acceptable anion derived from a salt of an inorganic acid or a salt of an organic acid.

16. The method of claim 1 wherein said acetylcholine esterase reactivator is administered in an amount within the range of from about 1 to 10 mg per 70 kg body weight.

17. The method of claim 1 wherein said active agent is selected from the group consisting of:

(a) a compound defined by the formula ($R^1$—CR=NOH)$^+$ X$^-$ where R is hydrogen, $C_{1-5}$ alkyl or NH$_2$, $R^1$ is $C_{1-5}$ alkyl and X$^-$ is a pharmaceutically acceptable anion derived from a salt of an inorganic acid or a salt of an organic acid;

(b) a compound defined by the formula ($R^1$—CR=NOH)$^+$ X$^-$ where R is hydrogen, $C_{1-5}$ alkyl or NH$_2$, $R^1$ is aryl and X$^-$ is a pharmaceutically acceptable anion derived from a salt of an inorganic acid or a salt of an organic acid;

(c) a compound defined by the formula ($R^1$—CR=NOH)$^+$ X$^-$ where R is hydrogen, $C_{1-5}$ alkyl or NH$_2$ and $R^1$ is a 5 or 6 membered heterocyclic moiety having from 1 to 3 nitrogen atoms in the heterocyclic ring and X⁻ is a pharmaceutically acceptable anion derived from a salt of an inorganic acid or a salt of an organic acid;

(d) a compound defined by the formula $R^1CR=NOH)^+ X^-$ where R is hydrogen, $C_{1-5}$ alkyl or $NH_2$ and $R^1$ is

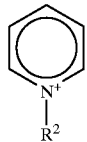

wherein $R^2$ is selected from the group consisting of:

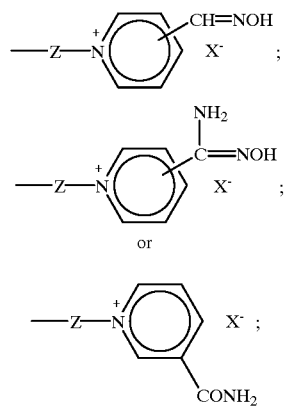

where Z is a polyalkylene group having from 1 to 6 carbon atoms, optionally including at least one ether linkage, or —(CH₂)n-phenyl-(CH₂)n— where n ranges from 1 to 6 and the phenyl moiety may be optionally substituted by $C_{1-5}$ alkyl, and wherein X⁻ is a pharmaceutically acceptable anion derived from a salt of an inorganic acid or a salt of an organic acid; and (e) mixtures thereof.

18. The method of claim 17 wherein said active agent is administered in a pharmaceutically acceptable carrier.

19. The method of claim 17 wherein said active agent is administered in combination with a stimulant.

20. The method of claim 19 wherein said stimulant is selected from the group consisting of nicotine, muscarine, arecoline, lobeline, cotinine, kat, nikethamide, ethamivan, bethanechol, pilocarpine, and mixtures thereof.

21. The method of claim 20 wherein said stimulant is nicotine.

22. The method of claim 17 wherein said active agent is administered in an amount within the range of from about 1 to 10 mg per 70 kg body weight.

23. The method of claim 1, wherein said active agent is selected from the group consisting of 2-pyridine aldoxime methiodide, 4-pyridine aldoxime methiodide, methyl-2-pyridyl ketoxime methiodide, 1-methyl-pyridinium-2-aldoxime, 2,3-butanedione-2-oxime, pyruvaldehyde aldoxime, 2-pyridine aldoxime methochloride, pralidoxime methylsulphate, obidoxime chloride, 1,1'-polymethylene bis (4-formylpyridinium) halide oximes, 1,1'-(2,5-dimethyl-p-phenylenedimethylene) bis (4-formylpyridinium) halide dioximes, 1,1'-polymethylene bis (3-formylpyridinium) halide dioximes, 1,1'-(p-phenylenedimethylene) bis (3-formylpyridinium) halide dioximes, bis quaternary 4-formylpyridinium halide monooximes, 1,1'trimethylene bis (3-amidooximopyridinium) halides, quaternary pyridine aldoxime, HI-6, diacetyl monoxime, 1,4-dimethyl-3-(hydroxyimino)methyl-1,2,4-triazolium chloride, 1-benzyl-3-(hydroxyimino)methyl-4-methyl-1,2,4-triazolium chloride, 3-(hydroxyimino)methyl-1-methyl-4-(2'-methylsulfonyl-1'-ethyl)-1,2,4-triazolium chloride, 1-([1'-(2'-butynyloxy)methyl]-2-(hydroxyimino)methyl-3-methylimidazolium chloride, 2-(hydroxyimino)methyl-3-methyl-1-[1'-2'-(methylsulfonyl)ethyloxy)methyl)-imidazolium chloride, 2-(hydroxyimino)methyl-3-methyl-1-[(2'-methyl-2'-nitropropyloxy)methyl]-imidazolium chloride, 1-[(2'-N,N-dimethylaminium)-1'-ethyl]2-(hydroxyimino)methyl-3-methylimidazolium chloride, 1-[2'-(hydroxyimino)methyl-3'-methyl-1'-imidazolo]-3-(4''-carbamoyl-1''-pyridino)propane dichloride, 1-(3'-bromopropyl-1'-oxy)methyl-2-(hydroxyimino)methyl-3-methylimidazolium chloride, 2-(hydroxyimino)methyl-3-methyl-1-(2'-pyridinium-1'-)ethylimidazolium chloride hydrochloride, 1-(3''-butynyl-1'-thio)methyl-2-(hydroxyimino)methyl-3-methylimidazolium chloride, and 1-[(2'-N-ethyl-N-trifluoromethane sulfonyl)amino-1'-]ethyl-2-hydroxyimino)methyl-3-methylimidazolium chloride.

24. The method of claim 17 wherein said tobacco is in the form of cigarettes.

25. The method of claim 17 wherein said tobacco is in the form of smokeless or chewing tobacco.

26. The method of claim 17 wherein said tobacco is in the form of pipe tobacco.

27. The method of claim 17 wherein said tobacco is in the form of cigars.

28. The method of claim 1 wherein said active agent is a prodrug derivative of a pyridinium aldoxime.

29. The method of claim 28 wherein active agent is administered in combination with a stimulant.

30. The method of claim 28 wherein said stimulant is selected from the group consisting of nicotine, muscarine, arecoline, lobeline, cotinine, kat, nikethamide, ethamivan, bethanechol, pilocarpine and mixtures thereof.

31. The method of claim 30 wherein said stimulant is nicotine.

32. The method of claim 28 wherein said active agent is administered in a pharmaceutically acceptable carrier.

* * * * *